(12) United States Patent
Giuliani et al.

(10) Patent No.: US 9,597,295 B2
(45) Date of Patent: *Mar. 21, 2017

(54) DIENE COMPOUNDS FOR USE IN HUMAN EPIDERMAL CELL REPAIR, AND PHARMACEUTICAL AND COSMETIC COMPOSITIONS CONTAINING THEM

(71) Applicant: GIULIANI S.P.A., Milan (IT)

(72) Inventors: Giammaria Giuliani, Milan (IT); Anna Benedusi, Milan (IT); Sergio Baroni, Villa D'adda (IT)

(73) Assignee: GIULIANI S.P.A., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/761,116

(22) Filed: Feb. 6, 2013

(65) Prior Publication Data
US 2013/0150443 A1    Jun. 13, 2013

Related U.S. Application Data

(63) Continuation of application No. 13/128,393, filed on May 9, 2011, now abandoned.

(30) Foreign Application Priority Data

Nov. 10, 2009   (WO) .................. PCT/EP2009/064880

(51) Int. Cl.
| | | |
|---|---|---|
| *A01N 37/06* | (2006.01) | |
| *A61K 31/22* | (2006.01) | |
| *A61K 31/045* | (2006.01) | |
| *A61K 31/11* | (2006.01) | |
| *A61K 31/231* | (2006.01) | |
| *A61K 31/232* | (2006.01) | |
| *A61K 8/34* | (2006.01) | |
| *A61K 8/36* | (2006.01) | |
| *A61K 8/37* | (2006.01) | |
| *A61K 31/202* | (2006.01) | |
| *A61K 31/23* | (2006.01) | |

(52) U.S. Cl.
CPC ............ *A61K 31/045* (2013.01); *A61K 8/342* (2013.01); *A61K 8/361* (2013.01); *A61K 8/37* (2013.01); *A61K 31/11* (2013.01); *A61K 31/202* (2013.01); *A61K 31/22* (2013.01); *A61K 31/23* (2013.01); *A61K 31/231* (2013.01); *A61K 31/232* (2013.01)

(58) Field of Classification Search
None
See application file for complete search history.

(56) References Cited

U.S. PATENT DOCUMENTS

| | | | |
|---|---|---|---|
| 3,959,491 A * | 5/1976 | Young et al. ................. | 514/775 |
| 3,962,311 A | 6/1976 | Loeliger | |
| 5,039,513 A * | 8/1991 | Chatterjee et al. ............. | 424/47 |
| 5,436,369 A | 7/1995 | Bronson et al. | |
| 5,605,894 A * | 2/1997 | Blank et al. ................... | 514/159 |
| 5,658,956 A * | 8/1997 | Martin et al. .................. | 514/724 |
| 2001/0019811 A1 | 9/2001 | Takanashi et al. | |
| 2005/0175555 A1* | 8/2005 | Stradi et al. .................... | 424/59 |

FOREIGN PATENT DOCUMENTS

| | | | |
|---|---|---|---|
| WO | WO 9600060 A1 * | 1/1996 | |
| WO | WO 03095403 | 11/2003 | |

OTHER PUBLICATIONS

Shimo et al., "Antimicrobial compounds for food preservation. I. Unsaturated fatty acids and their derivatives," Shokuhin Eiseigaku Zasshi (1966), 7(1), 55-59.*
Eastman, Sorbic Acid and Potassium Sorbate as Cosmetic Preservatives, Eastman Chemical Company (1998).*
Sauder et al., "Interleukin-1 enhances epidermal wound healing," Lymphokine Res. 1990 Winter;9(4):465-73.*
Coquette, A. et al., "Analysis of Interleukin-1α (IL-1α) and Interleukin-8 (IL-8) Expression and Release in in Vitro Reconstructed Human Epidermis for the Prediction of in Vivo Skin Irritation and/or Sensitization," Toxicology in Vitro 17 (2003) 311-321.
The User's Manual from the EC Regulation of European Commission—Health and Consumers—Sorbic Acid (Apr. 29, 2015).
The Handbook *Cosmetics and Dermatologic Problems and Solutions, Third Edition*, 2011 (1st edition:1990).
The User's Manual from the EC Regulation of European Commission—Health and Consumers (Mar. 6, 2015).
Pine E et al. "Biological activity of parrodienes, a new class of polyunsaturated linear aldehydes similar to carotenoids" Drugs Under Experimental and Clinical Research, Bioscience Ediprint Inc., XX, vol. 30, No. 5-6, Jan. 1, 2004, pp. 203-206.
Bissett D L et al. "Protective effect of topically applied conjugated hexadienes against ultraviolet radiation-induced chronic skin damage in the hairless mouse" Photodermatology, Photoimmunology & Photomedicine, Blackwell Publishing, vol. 7, No. 2, Apr. 1, 1990, pp. 63-67.

(Continued)

*Primary Examiner* — Jared D Barsky
(74) *Attorney, Agent, or Firm* — DLA Piper LLP (US); Stephanie X. Wang (57) ABSTRACT

The present invention relates to a novel use of compounds having the general formula (I):

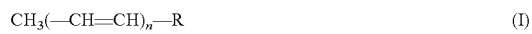

$$CH_3-(-CH=CH-)_n-R \qquad (I)$$

where n=from 2 to 7, and
R is chosen from among: CHO, $CH_2OH$, $CH_2O-CO-R'$, CO—OR', CO—O$^{(-)}$,
where R' is chosen from among H, the alkyl from $C_1$ to $C_{22}$,
each compound of general formula (I) being used as such or in a mixture,
as an active principle in a pharmaceutical or cosmetic composition to improve the human epidermal cell repair activity by means of the production of keratin mediated by the cytokeratins cK-19.

9 Claims, 3 Drawing Sheets

(56) References Cited

OTHER PUBLICATIONS

Lee Ping C. et al. "Short term feeding of hexadienal to postnatal rats: Effects on stomach aldehyde dehydrogenase" Biosis Host—Biosis, Jan. 13, 2003 (Jan. 13, 2003).
Rigano L et al. "Novel retinol-like actives from parrots feathers" IFSCC Magazine, Allured Pub., Carol Stream, IL, US, vol. 11, No. 4, Oct. 6, 2008, pp. 323-330.

* cited by examiner

DIENE COMPOUNDS FOR USE IN HUMAN EPIDERMAL CELL REPAIR, AND PHARMACEUTICAL AND COSMETIC COMPOSITIONS CONTAINING THEM

CROSS REFERENCES TO RELATED APPLICATIONS

This application is a continuation application of U.S. patent application Ser. No. 13/128,393 filed on May 9, 2011, which is a national stage entry of International Application No.: PCT/EP09/64880 filed on Nov. 10, 2009, which in turn claims priority to Italian Patent Application No. MI2008A001981 filed on Nov. 10, 2008; each of which is hereby incorporated by reference herein in its entirety.

FIELD OF THE INVENTION

Meshes of keratin filaments generally serve as a structural framework, providing mechanical support not only for individual cells, but also for whole epithelial layers. Keratins constitute a family of intermediate filament proteins that are assembled to form heterodimers of keratin type 1 (keratins 9 to 23) and keratin type 2 (keratins 1 to 8). Because of their dual, epithelial tissue type and differentiation-specific regulation, keratins are useful tools for studying epithelial differentiation by means of the specific mRNA expression profiles of the cytokeratins (cK mRNA).

PRIOR ART

Keratins type 1 and type 2 are coded by a multiple-gene family (each with more than 25 members) and they necessarily heteropolymerise one another to produce filaments of intermediate dimensions in the cytoplasm of epithelial cells (Hesse et al, 2000; Coulombe et al, 2001).

Keratins type I (K9-K21; Ha1-Ha8) range from 40 to 63 kDa and are more acidic.

Keratins type II (K1-K8; Hb1-Hb6) are larger (53-67 kDa) and more basic. K16 is rare or undetectable in intact human skin and is expressed together with the K6 isoforms in numerous complex epithelia, but there is no obvious correlation between its expression and any particular terminal differentiation programme or function of the epithelium.

K16 expression is strongly induced by acute challenges and in the context of diseases with aberrant epithelial differentiations. cK-16 is a marker of the early signs of skin irritation.

In adult human skin, K19 is limited to the external sheath at the root of the hair follicle and has not been detected in the epidermis. The particular location of cells positive for K19 in various epithelia has prompted the hypothesis that it may be a marker of the progenitors of the epithelium. In the skin, this idea was suggested on the strength of the presence of K19 in the "bulge area" of the hair follicle, where cells marked with 3H-thymidine have been identified. cK19 is expressed selectively in the skin by retinoic acid and its derivatives, indicating a role in promoting epithelial differentiation. cK10 to cK14 are markers of mitotic activity.

SUMMARY OF THE INVENTION

The present invention relates to a novel use of compounds having the general formula (I):

$$CH_3(-CH=CH)_n-R \quad (I)$$

where n=from 2 to 7, and
R is chosen from among: CHO, $CH_2OH$, $CH_2O-CO-R'$, $CO-OR'$, $CO-O^{(-)}$,
where R' is chosen from among H, the alkyl from $C_1$ to $C_{22}$, each compound of general formula (I) being used as such or in a mixture,
as an active principle in a pharmaceutical or cosmetic composition for improving its human epidermal cell repair activity through the keratin production mediated by the cK-19 cytokeratins.

An experimental study on epidermis reconstructed in vitro, reported in the following paragraphs of the present description, surprisingly showed an increase in cK-19 expression in the final differentiation of the epidermis treated with the compound according to the present invention.

The present invention relates also to any composition for the above-described use, in both the therapeutic and the cosmetic field, that includes the above-identified active principle and any suitable excipient, particularly for use on the skin.

The preferred compounds corresponding to the formula (I) for the use envisaged in the present invention are:
2,4,6-octatrien-1-ol (E,E,E), CAS #: 130971-00-5
2,4,6-octatrienoic acid (E,E,E), CAS #: 130971-00-5
2,4,6-octatrienoic acid sodium salt (E,E,E), CAS #: n/a
2,4,6-octatrienoic acid ethyl ester (E,E,E), CAS #5941-49-1
2,4,6-octatrienoic acid L-lysine salt, CAS #: n/a
2,4,6-octatrien-1-ol acetate (E,E,E), CAS #79541-79-0
2,4,6-octatrien-1-ol palmitate (E,E,E), CAS #: n/a The following examples illustrate the invention without limiting its scope in any way.

The characterisation data and the formulas for some of the compounds of general formula are given below (I).

$C_8H_{12}O$ mw 124.18
2E,4E,6E-Octatrien-1-ol
CAS #: 130971-00-5

$C_8H_{10}O_2$ mw 138.17
2E,4E,6E-Octa-2,4,6-trienoic acid
CAS #: 5205-32-3
Sodium salt: $C_8H_9O_2Na$ mw 160.15, CAS #: not available
Lysine salt: $C_8H_9O_2 \cdot C_6H_{15}N_2O_2$, mw 284.36, CAS #: not available $C_{10}H_{14}O_2$ mw 166.22
2E,4E,6E-Octa-2,4,6-trienoic acid ethyl ester
CAS #: 5941-49.1

$C_{10}H_{14}O_2$ mw 166.22
2,4,6-Octatrien-1-ol, acetate, (E,E,E)
CAS #: 79541-79-0

$C_{24}H_{42}O_2$ mw 362.60
2E,4E,6E-Octatrien-1-ol, palmitate
CAS #: not available The following are non-limiting examples of compositions particularly suitable for the above-stated use.

The quantities of the components are expressed as weight-to-weight percentages.

Example 1

| Acne gel | |
|---|---|
| INCI name | w/w % |
| Ammonium acryloyl dimethyltaurate/VP copolymer | 0.1-0.5 |
| PHOSAL 75 SA (lecithin, soybean in ethanol) | 2-4 |
| 2,4,6 octatrienoic acid | 0.05-0.3 |
| PEG-8 caprylic/capric glycerides | 0.1-0.3 |
| Sodium hydroxymethylglycinate | 0.4-0.5 |
| Lactic acid | q.s. pH 5 |
| Water q.s. | 100 |

Example 2

| Acne cleanser | |
|---|---|
| INCI name | w/w % |
| Disodium cocoamphodiacetate | 16-20 |
| Sodium lauroyl sarcosinate | 16-20 |
| 2,4,6 octatrienoic acid | 0.05-3 |
| Laureth-7 citrate | 1 |
| Decyl glucoside | 5 |
| CROVOL MARACUJA (PEG-60 *passiflora edulis* seed glycerides, PEG-60 *passiflora incarnata* seed glycerides) | 1-2 |
| Phenoxyethanol | 0.9 |
| PLANTSERVATIVE SWR (*lonicera caprifolium* extract, *lonicera japonica* extract, water) | 0.05-0.1 |
| Peg-120 methyl glucose dioleate | 1.26 |
| Panthenol | 0.4 |
| Dipotassium glycyrrhizate | 0.1-1 |
| Ammonium glycyrrhizate | 0.5-1.5 |
| Lactic acid | q.s. |
| Water q.s. | 100 |

Example 3

| Soothing body milk | |
|---|---|
| INCI name | w/w % |
| Allantoin | 0.35 |
| Disodium EDTA | 0.10-0.15 |
| Carbomer | 0.10-0.50 |
| L-lysine 2,4,6,octatrienoate | 0.05-0.30 |
| Sodium dehydroacetate | 0.20 |

-continued

| Soothing body milk | |
|---|---|
| INCI name | w/w % |
| Sorbityl furfural | 0.50-0.90 |
| Triethanolamine | 0.55 |
| PEG-8 beeswax | 8.00-15.00 |
| *Butyrospermum parkii* | 1.00-2.00 |
| Isostearyl isostearate | 5.00-10.00 |
| Caprylic/capric tryglyceride | 5.00-10.00 |
| Beta-sitosterol | 0.05-1.0 |
| Phenoxyethanol | 0.90 |
| Sodium hydroxymethylglycinate | 0.45 |
| Tocopherol | 0.20 |
| Ascorbyl palmitate | 0.003 |
| Glycyrrhetinic acid | 0.20-3.00 |
| Bisabolol | 0.20 |
| Perfume | 0.50 |
| Polymethylmethacrylate | 0.90 |
| Sodium hydroxide | q.s. |
| Lactic acid | q.s. |
| Water q.s. | 100.00 |

Example 4

| Acne body milk | |
|---|---|
| INCI name | % |
| Allantoin | 0.10-0.40 |
| Sodium EDTA | 0.15 |
| Carbomer | 0.10-0.50 |
| 2,4,6 octatrienoic acid | 0.05-0.3 |
| Sodium dehydroacetate | 0.20 |
| Sorbityl furfural | 0.50-0.90 |
| Triethanolamine | 0.40-0.60 |
| Peg-8 beeswax | 8.00-15.00 |
| *Butyrospermum parkii* | 1.00-2.00 |
| Isostearyl isostearate | 5.00-10.00 |
| Caprylic/capric tryglyceride | 5.00-10.00 |
| *Borago officinalis* | 1.00-3.00 |
| Beta-sitosterol | 0.05-1.0 |
| *Lonicera japonica* | 0.5 |
| Sodium hydroxymethylglycinate | 0.45 |
| Tocopherol | 0.2 |
| Ascorbyl palmitate | 0.003 |
| Glycyrrhetinic acid | 0.5 |
| Hydroviton (glycerine, sodium lactate, tea-lactate, serine, lactic acid, allantoin, urea, sorbitol) | 1 |

Acne body milk

| INCI name | % |
| --- | --- |
| Bisabolol | 0.2 |
| Perfume | 0.22 |
| Polymethylmethacrylate | 0.90 |
| Sodium hydroxide | q.s. |
| Lactic acid | q.s. |
| Water q.s. | 100.00 |

Example 5

Face cream for severe photoaging

| INCI name | w/w % |
| --- | --- |
| Tetrasodium glutamate diacetate | 0.1 |
| L-lysine 2,4,6 octatrienoate | 0.05-0.3 |
| Inositol | 0.8-0.12 |
| Glycerine | 1-2 |
| Betaine | 0.05-0.2 |
| Panthenol | 0.1 |
| Sodium hyaluronate | 0.003-0.01 |
| Xanthan gum | 0.09 |
| Ammonium acryloyl-dimethyltaurate/VP Copolymer) | 1.1 |
| *Persea gratissima* oil | 0.2-0.4 |
| Dicaprilyl carbonate | 0.8 |
| Pentaerythrityl tetra-di-t-butyl hydroxyhydrocinnamate | 0.05 |
| Hydrogenated lecithin | 0.1 |
| Stearic acid | 1 |
| Steareth-2 | 1.5 |
| Benzoic acid | 0.3 |
| Steareth-21 | 1 |
| Caprylyl glycol | 0.7 |
| Tocotrienols | 0.02 |
| Cyclopentasiloxane | 5-20 |
| Dimethicone | 0.5-2 |
| Polysilicone-11 | 1-3 |
| C30-45 alkyl cetearyl dimethicone crosspolymer | 1-2 |
| Polymethylmethacrylate | 0.9 |
| Sodium hydroxide | 0.1 |
| Ethanol | 4.5 |
| Lactic acid | q.s. |
| Water q.s. | 100 |

Example 6

Antiinflammatory cream

| INCI name | % P/P |
| --- | --- |
| Betain | 0.3-0.6 |
| Allantoin | 0.2-0.3 |
| Inositol | 0.5 |
| Trehalose | 0.2-0.3 |
| Glycerine | 2 |
| 2,4,6 octatrien-1-ol | 0.05-0.3 |
| Sorbityl furfural | 0.5-1 |
| Carbomer | 0.4 |
| Tetrasodium glutamate diacetate | 0.3 |
| PEG-8 Beeswax | 5-15 |
| *Butirospermum parkii* butter | 1-5 |
| Caprylic/capric triglyceride | 2-6 |
| Dicaprylyl ether | 2-6 |
| Isostearyl isostearate | 2-6 |
| Isopropyl sebacate | 2-6 |
| Ethylhexyl methoxycinnamate | 2-6 |
| Phenoxyethanol | 0.95 |
| Caprylyl glycol | 0.40 |

Antiinflammatory cream

| INCI name | % P/P |
| --- | --- |
| Hydrogenated lecithin | 0.200 |
| Glycyrrhetinic acid | 0.2-1.2 |
| Beta-sitosterol | 0.105 |
| Dimethylmethoxy chromanol | 0.02 |
| Diethylhexyl syringylidene malonate | 0.20 |
| Pentaerythrityl tetra-di-t-butyl hydroxyhydrocinnamate | 0.05 |
| *Calendula officinalis* extract | 2.00 |
| Tocotrienols | 0.005-0.01 |
| Bisabolol | 0.2-0.8 |
| Sodium hydroxide | q.s. |
| Lactic acid | q.s. |
| Perfume | 0.10-0.30 |
| Water q.s. | 100 |

Example 7

Soothing face cream

| INCI name | w/w % |
| --- | --- |
| Tetrasodium glutamate diacetate | 0.1 |
| 2,4,6 octatrienoic acid sodium salt | 0.05-0.3 |
| Inositol | 0.8-0.12 |
| Glycerine | 1.0-2.0 |
| Betaine | 0.05-0.2 |
| Panthenol | 0.10 |
| Sodium hyaluronate | 0.003-0.01 |
| Xanthan gum | 0.09 |
| Ammonium acryloyl-dimethyltaurate/VP copolymer | 0.8-2 |
| *Persea gratissima* oil | 0.2-0.4 |
| Dicaprilyl carbonate | 0.8 |
| Pentaerythrityl tetra-di-t-butyl hydroxyhydrocinnamate | 0.05 |
| Hydrogenated lecithin | 0.1 |
| Stearic acid | 0.5-2 |
| Steareth-2 | 1-3 |
| Phenoxyethanol | 0.9 |
| Steareth-21 | 1-3 |
| Caprylyl glycol | 0.5 |
| Tocotrienols | 0.02 |
| Cyclopentasiloxane | 5-20 |
| Dimethicone | 0.5-2 |
| Polysilicone-11 | 1-3 |
| C30-45 alkyl cetearyl dimethicone crosspolymer | 1-3 |
| Polymethylmethacrylate | 0.5-1 |
| Water | 10 |
| Sodium hydroxide | 0.1 |
| Lactic acid | q.s. |
| Water q.s. | 100 |

Example 8

Antiwrinkle face cream

| INCI name | w/w % |
| --- | --- |
| Tetrasodium glutamate diacetate | 0.1 |
| 2,4,6 octatrien-1-ol | 0.05-0.3 |
| Inositol | 0.8-0.12 |
| Glycerinee | 1-2 |
| Betaine | 0.05-0.2 |
| Panthenol | 0.1 |
| Sodium hyaluronate | 0.003-0.01 |
| Xanthan gum | 0.05-0.5 |
| Carbomer | 0.2-1 |
| Caprilyc/capric triglycerides | 4-8 |
| Squalane | 1-2 |

-continued

| Antiwrinkle face cream | |
|---|---|
| INCI name | w/w % |
| Paraffinum liquidum | 1-2 |
| Dimethicone | 1-2 |
| Cyclopentasiloxane | 1-3 |
| Hydrogenated lecithin | 0.10-1 |
| Phenoxyethanol | 0.9 |
| Sodium hydroxymethylglycinate | 0.45 |
| PEG-8 beeswax | 8-15 |
| Tocotrienols | 0.02 |
| Sodium hydroxide | q.s. |
| Lactic acid | q.s. |
| Water q.s. | 100 |

A study was conducted as described below, with reference to the figures in the attached drawings, to demonstrate the effect on the epidermis of the compounds of the present invention.

DETAILED DESCRIPTION OF THE INVENTION

Experimental Study

1. Introduction and Aims 3D human tissue cultures, such as reconstructed human epidermis (RHE), were used for their tissue functionality and multilayered structure, as in vivo, which takes penetration and tissue absorption into account.

They have been recognised as suitable and sensitive models for biological research on the skin and for compatibility tests with a view to replacing the use of experimental animals and also so as to improve the prediction of the irritative power of substances in relation to tests on humans (ECVAM-Atla 33 Suppl 1, 47-81-2005).

The aim of the present study was to test the activity on cell repair and the toxic effects in RHE, starting from 11 days and for up to 17 days of differentiation, based on the expression of the following specific cytokeratins:

cK-16, as a marker of cytokeratin activation and inflammation;
cK-19, to assess the activity and role of the compounds being tested;
cK-14, as a marker of mitotic activity at basal level.

The expression of these three genes was assessed by mRNA quantification using RT-PCR and immunohistochemistry (for cK19 and cK16).

The release of IL-1α was monitored during the study as a complementary parameter for defining proper cell renewal.

2. Experimental Design 2.1 Instruments and Reagents
Mettler Toledo balance S 204 01 g
$CO_2$ incubator NuAir
DMSO Sigma (batch D5879)
Phospate buffer saline solution—PBS Fluka (batch 79382)
10% buffered formalin—Sigma (HT 50-1-128)

2.2. Experimental Model

The RHE (SkinEthic®) 0.5 $cm^2$, which reproduces the morphology of the epidermis, was accurately characterised: a fully-differentiated epidermis develops after 17 days of airlift culture of NHK (normal human keratinocytes) from skin biopsies in a given medium (MCDB153).

A good barrier function, good intra-batch reproducibility and low variability in terms of permeability to the test molecules have been reported in the literature when compared with ex-vivo human models.

2.2 Experimental Conditions

The tissues were produced in accordance with clearly-defined quality assurance procedures (ISO certification 9002).

All the biological components of the epidermis and the growth medium kit were tested for any presence of viruses, bacteria and mycoplasma.

The quality of the end-product was ascertained by means of an MTT cytotoxicity test with sodium dodecyl sulphate (SDS).

On arrival, the RHE (day 11) were removed from the agarose nutrient solution under a flow of sterile air. The inserts were rapidly plated in six-well plates previously filled with 1 ml of growth medium each at 37° C., 0.5% $CO_2$, and 90% relative humidity, taking care to avoid any formation of bubbles underneath the insert.

The study began 24 hours after the arrival of the RHE (day 12).

The growth medium used during the study was replaced every 24 hours.

3. Substances Tested

The following compounds according to the present invention were chosen as the substances to test:
2,4,6-octatrien-1-ol
2,4,6-octatrienoic acid ethyl ester (ethyl octatrienoate).

| Substance tested | 2,4,6-octatrien-1-ol | Ethyl octatrienoate |
|---|---|---|
| Quantity | 1 g | 2 g |
| Identification code | PRT 268/4 | DPRT 268 BIS |
| Batch | AMP 268/4 | 268 bis |
| Storage | −20° C. ± 2° C. | −20° C. ± 2° C. |
| Supplier | GIULIANI SpA | GIULIANI SpA |
| Dose | 0.1% | 0.1% |

3.1 Dosage and Exposure

The substances tested were solubilised in DMSO (Sigma) to obtain a final concentration of 0.2%.

This stock solution was diluted in PBS to achieve the 0.1% of active principle.

The solutions were stored at −20° C. until the test.

The solution was applied with care to each tissue using a micro-pipette in a single dose of 20 µl.

3.2 Controls

As a positive control, we considered retinol, applied using the same procedure as for the substances being tested (20 µl).

The negative controls were:
1 RHE treated with DMSO in PBS
1 RHE treated with PBS

| Name | Retinol |
|---|---|
| Quantity | 1 g |
| Identification code | RET |
| Batch | R7632 |
| Storage | −20° C. ± 2° C. |
| Dose | 0.1% |
| Supplier | Sigma |

4. Methods 4.1 Histology and Immunohistochemistry
Rationale

Histology is an important complementary parameter in all in vitro studies on reconstructed tissues, enabling the biochemical and molecular results to be confirmed. In the case of the skin repair process, histology can provide quantitative information on skin compatibility and tissue remodelling.

Immunohistochemistry enables a quantitative assessment of protein expression.

Materials
Leica microscope DM 2500—20×
10% formalin—Sigma

Procedure

At the end of the study period, the tissues were washed with PBC, fixed in 10% buffered formalin and prepared for histological examination.

The tissue was embedded in paraffin blocks and cut into sections (3-5µ thick) on a microtome. The sections were then transferred to slides, deparaffinised and rehydrated, then stained with haematoxylin and eosin (H&E).

For immunohistochemistry, antigen retrieval was done with the Cooker method in 10 nM of citrate buffer with a pH=6.

Antibodies:
cK16: mouse monoclonal antibody, clone LL025 (Neo Markers USA)
cK19: mouse monoclonal antibody, clone Ks 19.1 (Neo Markers USA
Signal amplification—Polymer (Labvision USA)
Enzyme: oxidase (HRP)
Chromogen: DAB (Dako)
Counterstaining: haematoxylin (Merck)

4.2 Real-Time PCR
4.2.1 RNA Extraction
Materials
RNAqueous kit (AMBION)
Rationale The RNAcqueous method is a system used to isolate DNA based on rapid filtering with no phenols.

The method is based on the capacity of the glass fibres to bind the nucleic acid in chaotropic concentrated saline solutions. The samples are disrupted in a highly-concentrated solution of guanidinium salts that lyse the cells and inactivate the endogenous RNase. The lysate is diluted with ethanol to make the DNA competent for binding with the glass fibre of the filter in the filter cartridge. The RNA binds to the filter, while the other cell components slide freely through the filter. The filter is then washed three times and the RNA is eluted in a solution with a very low ionic strength.

4.2.2 cDNA Reverse Transcription
Materials
high-capacity cDNA reverse transcription kit (Applied Biosystems)
Rationale The rationale in this method is based on the use of random primers to begin cDNA synthesis that ensure an efficient synthesis of the first helix of all the RNA molecules present.

The cDNA is diluted and stored at −20° C.

4.2.3. Real-Time PCR
Rationale

The "Applied Biosystems 7500 real-time PCR" instrument uses PCR chemistry based on fluorescence, the TaqMan assay.

This technique uses Taqman probes to identify the fluorescent signal: it is highly sensitive and consists in amplifying and quantifying a specific nucleic acid sequence. The PCR product is detected in real time. The DNA, cDNA or RNA are quantified by determining the cycle in which the PCR product can be identified first, and therefore not when the reaction has reached saturation. The product is quantified by detecting the fluorescence measured in each cycle: the entity of the signal is directly proportional to the quantity of product amplified.

The relative quantification is measured from the difference between the expression of the nucleic acid sequence of a sample being tested and the same sequence in the calibration sample.

Gene expression is the process by which the transmissible information in a gene, such as a DNA sequence, is transformed into the functional product of the gene, i.e. a protein or RNA.

The expression of many genes is regulated after transcription, so an increase in the concentration of the mRNA does not always determine an increase in the expression of the protein. That is why it is important to study mRNA. Gene regulation gives the cells control over structure and function. Controlling the timing, site and quantity of gene expression can have a profound effect on the gene's function (actions) in the body.

The method for measuring the abundance of mRNA is RT-PCR (real-time polymerase chain reaction). The low level of noise in the data obtained by RT-PCR often makes it the method of choice for assessing gene expression.

Materials
2× TaqMan Universal PCR Master Mix
20× Taqman gene expression assay
"nuclease free" water
GAPDH (endogenous control) Hs 99999905_1
target genes:

| Target genes | Taqman codes |
|---|---|
| KRT 14 | Hs00559328_m1 |
| KRT16 | Hs00373910_g1 |
| KRT19 | Hs00761767_s1 |

Procedure

Each biological sample was processed in triplicate. The Taqman gene expression assay and cDNA (25 ng) were added to the "2× TaqMan Universal PCR Master Mix", making up to a total volume of 25 µl.

The steps in the PRISM reactor 7500 were:

| Conditions | STEP 1: AmpliTaq Gold DNA polymerase activation | STEP 2: 40 cycles | |
|---|---|---|---|
| Temperature | 95° C. | 95° C. | 60° C. |
| Time | 10 MIN | 15 SEC | 1 MIN |

4.2.4 Sample Preparation for RT-PCR Analysis

The tissues were homogenised in 300 µl of lysis buffer for DNA extraction.

4.3 IL-1α Quantification in the Growth Medium Using ELISA.

Rationale

Interleukin 1-α is recognized as an early sign of inflammation.

The release of IL-1α was assayed in 200 µl of the growth medium underneath the RHE at preset sampling times using a highly-sensitive, specific ELISA (enzyme-linked immunosorbent assay) kit according to the manufacturer's instructions. The end-product was quantified at 450 nm.

The underlying growth medium for each RHE was collected immediately after the recovery time and stored at −20° C. in plastic cryo-vials.

Before the test, the medium was conditioned at room temperature. The results were expressed as pg/ml of IL-1α. Concentrations between 3.9 and 250 pg/ml were considered within the range of sensitivity.

Materials

Quantikine® kit (R&D Systems) Code DLA 50 (IL-1)
Growth medium—SkinEthic
Microplate Autoreader M-100 Infinite Tecan 5. Procedure The times and the analysis are shown in Table I.

Each day, at the established time, the corresponding samples were processed for analysis as explained in the Methods.

TABLE I

|  | Day 13 24 h | Day 15 48 h | Day 17 120 h |
|---|---|---|---|
| Negative control | RT-PCR | RT-PCR + IMMUNO-HISTO | RT-PCR + IMMUNO-HISTO |
| Positive control | RT-PCR | RT-PCR + IMMUNO-HISTO | RT-PCR + IMMUNO-HISTO |
| Substances tested | RT-PCR | RT-PCR + IMMUNO-HISTO | RT-PCR + IMMUNO-HISTO |
| ELISA IL-1 α | All | All | All |

Day 1—Application of the Product

On day 1, the RHE were 12 days old. The substances being tested (in duplicate) and the controls were applied in a single dose (20 µl). The RHE were then incubated without further treatment for 24 hours.

Day 2—24 h of Treatment

The growth medium was changed every day and collected and stored at −20° C. for further analysis.

The samples corresponding to the 24-hour treatment were processed and analysed (see Table I).

Day 4—48 h of Treatment

The growth medium was changed every day and collected and stored at −20° C. for further analysis.

The samples corresponding to 48 hours of treatment were processed and analysed (see Table I).

Day 6—120 h of Treatment

The growth medium was changed every day and collected and stored at −20° C. for further analyses.

The samples corresponding to 120 hours of treatment were processed and analysed (see Table I).

6. Data Collection and Interpretation

The data generated by the analyses were recorded directly by the in-house software SDS 1.3.1 and recorded as raw relative quantitative data.

The results were exported in Excel.

A value was accepted when the gene increased by ±1SD by comparison with the calibration sample.

The samples for histology were analysed under the microscope. The overall morphology and any changes by comparison with the negative controls were assessed and recorded in the laboratory report.

The samples for histology were analysed under the Leica microscope DM2500 and recorded using the Leica Application Suite (LAS) software.

6. Results

The controls with DMSO differed in terms of cK19 expression from the control with PBS: the results were generated using the controls with DMSO for calibration and are shown in the attached graphs.

Figure 1:
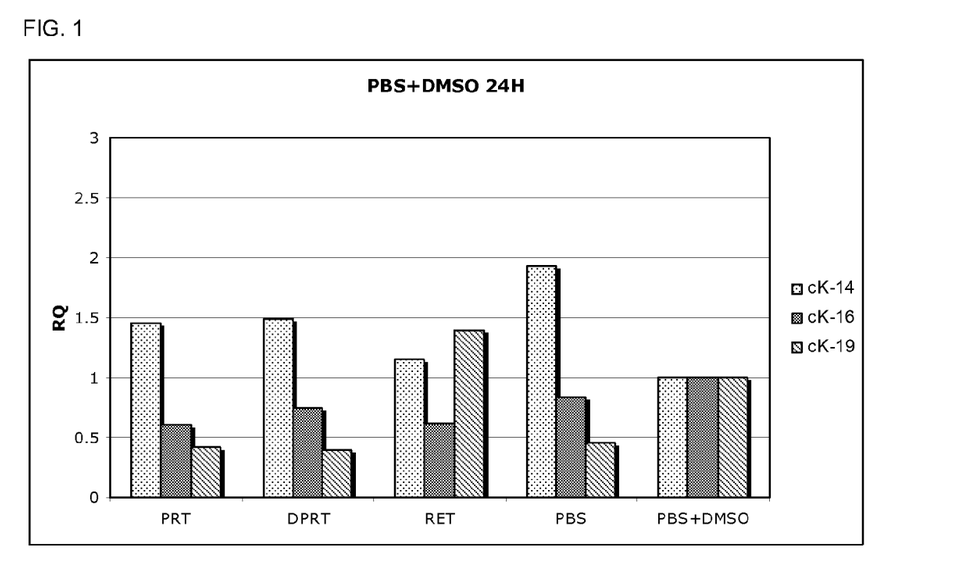
FIG. 1 shows the mRNA gene expression 24 hours after the treatment, in reconstructed human epidermis (RHE) on day 13.

FIG. 1 shows the mRNA gene expression in the RHE after 24 hours of treatment, on day 13, for the substances being tested and the controls (see the identification codes above).

cK-14 was found significantly increased in the PBS controls by comparison with the PBS+DMSO controls.

After 24 hours, there was no evidence of any significant cK-16 expression. cK-19 was much diminished in the samples treated with PRT and DPRT, unlike the RET (positive control) which showed a regulation level resembling the values of the calibrator.

Figure 2:
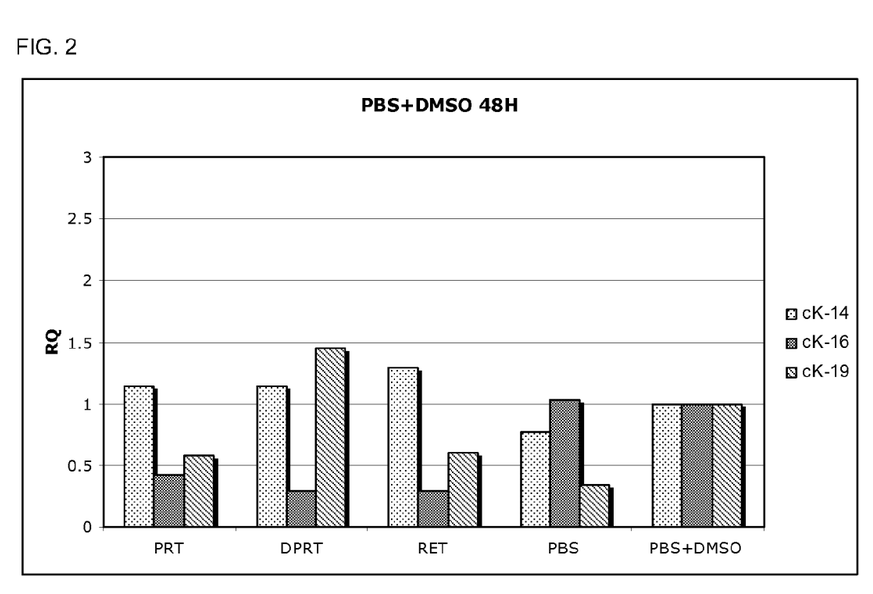
FIG. 2 shows the mRNA gene expression 48 hours after the treatment, in RHE on day 15.

FIG. 2 shows the mRNA gene expression in the RHE after 48 hours of treatment, on day 15.

There was no significant variation in the cK-14 induced by the treatments with respect to the PBS control.

cK-19 was found diminished for both RET and PRT treatments by comparison with the PBS control, whereas the gene's expression was not diminished after treatment with DPRT.

The cK-16 gene expression was found lower by comparison with the controls after treatment with all three substances being tested.

Figure 3:
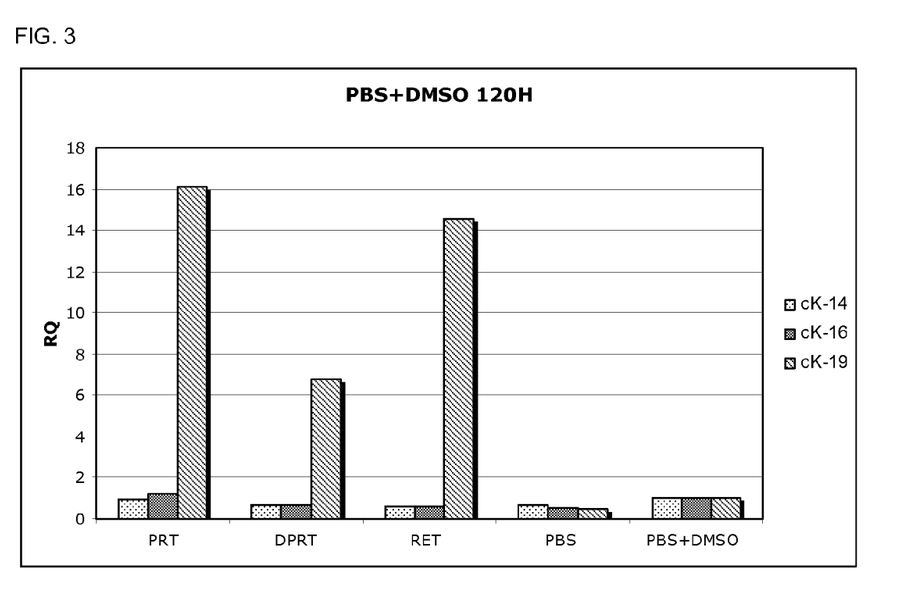
FIG. 3 shows the mRNA gene expression 120 hours after the treatment, in RHE on day 17; as explained in more detail below, in relation to this study, and particularly in the "Results".

FIG. 3 shows the mRNA gene expression in the RHE after 120 hours of treatment, on day 17.

At the end of the treatment, corresponding to the final differentiation of the RHE, no significant changes were found in cK14 and cK-16 expression, whereas the cK-19 expression had increased significantly in the treated tissues by comparison with the controls.

PRT induced an increase comparable with that of the RET positive control.

The release of IL-1α was also monitored to study the long-term effect on inflammatory status. The results showed:
  after 24 h, an early but very low release of IL-1α after treatment with RET, but no such release for PRT or DPRT;
  after 48 h, a significant IL-1α release for both PRT and RET, and for the DMSO control;

after 120 h, only the DMSO control (0.2%) showed a marked release of the cytokine.

IL-1α has to be correlated with the histological results, on the one hand, and with the mechanism of action of the retinoids on the other: the results after 48 hours correlate and confirm the histological observations (tissue damage corresponding to a high release of IL-1α), but after 120 hours the lack of any IL-1α release for RET and PRT is explained by the absence of live cells (necrotic tissue, as shown in the H&E histology and confirmed by the activation of cK-16). The release of IL-1α after treatment with retinoids has a functional significance at skin level. The retinoids (particularly after treatment with retinoic acid) have a pro-inflammatory effect through the release of IL-1α by the basal keratinocytes, but this event is also linked to an indirect epidermal growth promoting activity. This behaviour has been confirmed in the RHE model (Experimental Dermatology 2002, 11; 59-74 Bernard F. X. et al.) and it seems that this IL-1α message correlates not with the cK, but with the cells underneath, such as the dermal fibroblasts.

TABLE II

Histology and immunohistochemistry: pooled for two exposures, after 48 hours and 120 hours

| | H&E | cK-16 | | | cK-19 |
|---|---|---|---|---|---|
| PRT | necrotic tissue | necrotic tissue | +++ | +++ | + | – |
| DPRT | some signs of toxicity at basal level | signs of necrosis at suprabasal level, loss of specific staining | – | +/– | – | – |
| RET | normal morphology | signs of necrosis at suprabasal level, loss of specific staining | + | + | –/+ | – |
| CN | highly differentiated corneal layer, eosinophils observed in the lamellar structure epidermal keratinocytes (Kc) detectable with basophilic cytoplasm and normal euchromatic nuclei the three layers (basal, spinal and granular) are clearly distinguishable numerous keratohyaline granules contained in the granular layer | – | –– | – | – |

It is important to emphasise that differences emerged in the analysis of the same treatment, even in the same vertical section.

The epidermal differentiation on day 17 after the various treatments was satisfactory when compared with the control.

The immunohistochemical results are consistent with the transcriptional study of cK-16 expression.

Conversely, no cK-19 expression was observed when the comparison was drawn with the RT-PCR results in the immunolocalisation at the most important time, i.e. on day 17: the explanation for these findings lies in the morphological changes (many necrotic cells) that occurred in the treated tissue, which can influence the transductional response.

7. Conclusions

The above-described study was conducted on an in vitro model of human epidermis to ascertain the activity of two compounds according to the present invention, as defined in section 3.3 "Substances tested" above. It showed:

on histomorphological analysis, the expression of cK-16 and the localisation of the IL-1α release denote a toxicity similar for retinol and 2,4,6-octatrien-1-ol after a single acute administration at the concentration considered (0.1%), whereas ethyl octatrienoate showed no relevant signs of toxicity;

the expression of cK-14 did not differ significantly during the study by comparison with the controls, indicating that mitotic activity was not influenced by the treatment with the two compounds according to the present invention, or with retinol;

the transcriptional study on cK-19 expression showed an up-regulation of cK-19 in the final differentiation of the reconstructed human epidermis in vitro (RHE on day 17) after treatment with retinol, 2,4,6-octatrien-1-ol, or ethyl octatrienoate. This provides significant evidence of the cell repair activity of the compounds according to the present invention;

the results of RT-PCR were not confirmed by the immunohistochemical findings for the reasons previously discussed in the Results. cK-10 expression in the RHE Finally, in a separate study conducted using similar methods, the expression of cK-10 in the RHE was studied on days 15 and 17 of differentiation, recorded by its immunohistochemical expression. cK-10 is a marker of the terminal differentiation of the keratinocytes at granular and spinal level.

The result showed that, on day 17, the expression was stronger for the 2,4,6-octatrien-1-ol treated sample than for the untreated controls, and negative for the retinol sample, confirming the superior activity of the compounds according to the present invention.

The invention claimed is:

1. A method of increasing keratin production in human epidermis cells, comprising:
topically administering to a subject in need thereof an effective amount of a composition consisting of a sole active principle having general formula (I) and at least one pharmaceutically acceptable excipient:

CH₃(—CH═CH)$_n$—R     (I)

wherein n=3-7,
R is selected among: CH$_2$O—CO—R', CO—OR', CO—O$^{(-)}$,
wherein R' is selected among H, alkyl from C$_1$ to C$_{22}$,
wherein the sole active principle increases cytokeratins cK-19 without irritation or signs of toxicity.

2. The method according to claim 1, wherein the sole active principle is 2,4,6-octatrienoic acid.

3. The method according to claim 1, wherein the sole active principle is a pharmacologically or cosmetically acceptable salt of 2,4,6-octatrienoic acid.

4. The method according to claim 1, wherein the sole active principle is 2,4,6-octatrienoic acid sodium salt.

5. The method according to claim 1, wherein the sole active principle is 2,4,6-octatrienoic acid L-lysine salt.

6. The method according to claim 1, wherein the sole active principle is 2,4,6-octatrienoic acid ethylester.

7. The method according to claim 1, wherein the sole active principle is a mixture of two or more of the compounds of formula (I).

8. The method according to claim 1, wherein said composition comprises an amount of the sole active principle in the range 0.05-0.3% by weight.

9. The method according to claim 1, wherein said composition comprises the sole active principle with any suitable excipient for a topical administration onto the skin.

* * * * *